(12) United States Patent
Bihorac et al.

(10) Patent No.: US 12,014,832 B2
(45) Date of Patent: Jun. 18, 2024

(54) METHOD AND APPARATUS FOR PREDICTION OF COMPLICATIONS AFTER SURGERY

(71) Applicant: UNIVERSITY OF FLORIDA RESEARCH FOUNDATION, INCORPORATED, Gainesville, FL (US)

(72) Inventors: Azra Bihorac, Gainesville, FL (US); Xiaolin Li, Gainesville, FL (US); Parisa Rashidi, Gainesville, FL (US); Panagote Pardalos, Gainesville, FL (US); Tezcan Ozrazgat-Baslanti, Gainesville, FL (US); Wiliam Hogan, Gainesville, FL (US); Daisy Zhe Wang, Gainesville, FL (US); Petar Momcilovic, Gainesville, FL (US); Gloria Lipori, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 352 days.

(21) Appl. No.: 16/616,534

(22) PCT Filed: Jun. 1, 2018

(86) PCT No.: PCT/IB2018/053956
§ 371 (c)(1),
(2) Date: Nov. 25, 2019

(87) PCT Pub. No.: WO2018/220600
PCT Pub. Date: Dec. 6, 2018

(65) Prior Publication Data
US 2020/0161000 A1 May 21, 2020

Related U.S. Application Data

(60) Provisional application No. 62/651,402, filed on Apr. 2, 2018, provisional application No. 62/514,473, filed on Jun. 2, 2017.

(51) Int. Cl.
G16H 50/30 (2018.01)
G06N 7/01 (2023.01)
G16H 10/60 (2018.01)
G16H 20/40 (2018.01)

(52) U.S. Cl.
CPC .............. G16H 50/30 (2018.01); G06N 7/01 (2023.01); G16H 10/60 (2018.01); G16H 20/40 (2018.01)

(58) Field of Classification Search
CPC ......... G16H 50/30; G16H 20/40; G16H 10/60
See application file for complete search history.

(56) References Cited

U.S. PATENT DOCUMENTS

| | | | |
|---|---|---|---|
| 8,515,777 B1 * | 8/2013 | Rajasenan | G16H 50/30 |
| | | | 705/7.14 |
| 9,946,840 B1 * | 4/2018 | Kemp | G16H 50/30 |

(Continued)

FOREIGN PATENT DOCUMENTS

| | | | |
|---|---|---|---|
| WO | WO-2017/037581 A1 | 3/2017 | |
| WO | WO-2017037581 A1 * | 3/2017 | ............. G06F 19/00 |

OTHER PUBLICATIONS

Jonathan L. French, "Generalized additive models for cancer mapping with incomplete covariates", 2004, pp. 177-191 (Year: 2004).*

(Continued)

*Primary Examiner* — Rajesh Khattar
*Assistant Examiner* — Steven G. S. Sanghera
(74) *Attorney, Agent, or Firm* — Alston & Bird LLP (57) ABSTRACT

Methods and systems disclosed herein utilize an automated analytics framework to implement a perioperative complication risk algorithm that uses existing clinical data in electronic health records to forecast patient-level probabilistic risk scores for eight major postoperative complications. An example method includes accessing health record data for a patient, normalizing the accessed health record (Continued)

data to generate a health record data set for the patient, transforming one or more features from the health record data set, selecting one or more transformed features from the health record data set, calculating risk probabilities for one or more complication risk categories based on the health record data set and the selected one or more features, calculating mortality risk probabilities for one or more mortality risk categories based on the calculated risk probabilities, and generating a personalized risk panel based on the calculated risk probabilities and the calculated mortality risk probabilities.

20 Claims, 6 Drawing Sheets

(56) References Cited

U.S. PATENT DOCUMENTS

| | | | | |
|---|---|---|---|---|
| 2004/0172307 | A1* | 9/2004 | Gruber | G06Q 10/10 705/3 |
| 2005/0182655 | A1* | 8/2005 | Merzlak | G16H 50/70 705/2 |
| 2012/0239375 | A1* | 9/2012 | Laxmanan | G06Q 10/06 703/22 |
| 2013/0185097 | A1* | 7/2013 | Saria | G06Q 10/00 705/3 |
| 2014/0058743 | A1* | 2/2014 | Snider | G16H 50/30 705/2 |
| 2015/0264507 | A1* | 9/2015 | Francombe | H04S 7/301 381/303 |
| 2016/0292241 | A1* | 10/2016 | Patterson | G16H 10/60 |
| 2017/0185727 | A1* | 6/2017 | Harris | G06N 5/04 |
| 2018/0315507 | A1* | 11/2018 | Mortazavi | G16H 50/30 |
| 2019/0028367 | A1* | 1/2019 | Tippenhauer | H04L 41/142 |
| 2019/0096528 | A1* | 3/2019 | Murphy | G06F 3/0482 |

OTHER PUBLICATIONS

International Searching Authority, International Search and Written Opinion for International Application No. PCT/IB2018/053956, Aug. 13, 2018, (17 pages), Rijswijk, The Netherlands.

* cited by examiner

METHOD AND APPARATUS FOR PREDICTION OF COMPLICATIONS AFTER SURGERY

CROSS REFERENCE TO RELATED APPLICATIONS

This application is a National Stage Application, filed under 35 U.S.C. § 371, of International Application No. PCT/IB2018/053956, filed Jun. 1, 2018, which claims priority to U.S. Provisional Application No. 62/514,473, filed Jun. 2, 2017, and U.S. Provisional Application No. 62/651,402, filed Apr. 2, 2018, which are hereby incorporated herein in their entireties by reference.

STATEMENT REGARDING FEDERALLY SPONSORED RESEARCH OR DEVELOPMENT

This invention was made with government support under R01 GM110240 awarded by National Institutes of Health. The government has certain rights in the invention.

BACKGROUND

Each year 1.5 million patients develop a major complication after surgery. Between 2005 and 2013, the average number of surgical procedures performed annually worldwide increased by 33.6%, with a total of 312 million procedures reported in the year 2012 alone. Surgical complications have been shown to increase postoperative morbidity and mortality, with a reported five-fold increase in the median cost of inpatient hospitalization following major surgery. Postoperative complications (PC) cause a two-fold increase in the 30-day mortality cost and are associated with long-term health consequences. Thus, there is a need in the art for methods, apparatuses, systems, computing devices, and/or the like that enable the identification of patients at the highest risk for developing a major PC, which in turn would allow the clinician to utilize management strategies to prevent such complications.

BRIEF SUMMARY

To meet this need and others, example embodiments of the present invention provide methods, apparatus, systems, computing devices, computing entities, and/or the like for predicting complications after surgery. In this regard, example embodiments utilize an automated analytics framework to implement a perioperative risk algorithm that uses existing clinical data in electronic health records to forecast patient-level probabilistic risk scores for eight major postoperative complications. Some of these example embodiments may thereafter determine patient-level mortality probabilities using the calculated risk scores. Methods, systems, and computer program products are described herein that are configured to provide a real-time intelligent perioperative learning system or otherwise known as a surgery risk analytics platform that periodically collects the electronic health record (EHR) data of patients, and performs data integration, variable generation, surgical risk scores prediction, and risk scores visualization.

In example embodiments, various systems, methods, and computer program products are provided for evaluating surgical risk and providing a surgery risk analytics platform service. An example method includes accessing health record data for a patient, normalizing the accessed health record data to generate a health record data set for the patient, transforming one or more features from the health record data set, selecting one or more transformed features from the health record data set, calculating risk probabilities for one or more complication risk categories based on the health record data set and the selected one or more features, calculating mortality risk probabilities for one or more mortality risk categories based on the calculated risk probabilities, and generating a personalized risk panel based on the calculated risk probabilities and the calculated mortality risk probabilities. The personalized risk panel comprises a list of features contributing to the calculated risk probabilities.

In some example embodiments, transforming the one or more features from the health record data set comprises remodeling raw features based on a plurality of predefined dictionaries for use in one or more predictive models.

In some example embodiments, the method may include removing one or more outliers from the health record data, replacing one or more missing variables of the health record data with replacement data, and normalizing the health record data to generate a health record data set for the patient. In some example embodiments, the one or more features from the health record data set are at least one of perioperative demographic, socio-economic, administrative, clinical, pharmacy, and laboratory variables.

In some example embodiments, the method may include using a generalized additive model (GAM) with logistic link function in calculating the risk probabilities for one or more complication risk categories and categorizing the complication risk categories based on the GAM. The method may further include applying a random forests classifier over the calculated risk probabilities to identify probability of death at one, three, six, twelve, and twenty four months after surgery.

Although described using an example method above, a surgery risk analytics platform for surgical risk evaluation based on a surgery risk analytics platform service is also contemplated herein that includes at least a processor and a memory having computer coded instructions therein that, when executed by the processor, cause the surgery risk analytics platform to: access health record data for a patient, normalize, by a data transformer module of the surgery risk analytics platform, the accessed health record data to generate a health record data set for the patient, transform, using the data transformer module, one or more features from the health record data set, select, using the data transformer module, one or more transformed features from the health record data set, calculate, using a data analytics module surgery risk analytics platform, risk probabilities for one or more complication risk categories based on the health record data set and the selected one or more features, calculate, using the data analytics module, mortality risk probabilities for one or more mortality risk categories based on the calculated risk probabilities, and generate a personalized risk panel based on the calculated risk probabilities and the calculated mortality risk probabilities.

In some example embodiments, the surgery risk analytics platform may further remove one or more outliers from the health record data, replace one or more missing variables of the health record data with replacement data, and normalize the health record data to generate a health record data set for the patient. In some example embodiments, the one or more features from the health record data set are at least one of perioperative demographic, socio-economic, administrative, clinical, pharmacy, and laboratory variables.

In some example embodiments, the surgery risk analytics platform may further use a generalized additive model (GAM) with logistic link function in calculating the risk probabilities for one or more complication risk categories and categorize the complication risk categories based on the GAM. The surgery risk analytics platform may further apply a random forests classifier over the calculated risk probabilities to identify probability of death at one, three, six, twelve, and twenty four months after surgery.

Similarly, an example computer program product is also contemplated herein. The computer program product includes at least one non-transitory computer-readable storage medium having computer-executable program code portions stored therein, the computer-executable program code portions comprising program code instructions for accessing health record data for a patient, normalizing the accessed health record data to generate a health record data set for the patient, transforming one or more features from the health record data set, selecting one or more transformed features from the health record data set, calculating risk probabilities for one or more complication risk categories based on the health record data set and the selected one or more features, calculating mortality risk probabilities for one or more mortality risk categories based on the calculated risk probabilities, and generating a personalized risk panel based on the calculated risk probabilities and the calculated mortality risk probabilities.

In some example embodiments, the computer program product is caused to remove one or more outliers from the health record data, replace one or more missing variables of the health record data with replacement data, and normalize the health record data to generate a health record data set for the patient. In some example embodiments, the one or more features from the health record data set are at least one of perioperative demographic, socio-economic, administrative, clinical, pharmacy, and laboratory variables.

In some example embodiments, the computer program product may further use a generalized additive model (GAM) with logistic link function in calculating the risk probabilities for one or more complication risk categories and categorize the complication risk categories based on the GAM. The surgery risk analytics platform may further apply a random forests classifier over the calculated risk probabilities to identify probability of death at one, three, six, twelve, and twenty four months after surgery.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having thus described the invention in general terms, reference will now be made to the accompanying drawings, which are not necessarily drawn to scale.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

Overview

Systems and methods described herein are configured to transform or otherwise manipulate a general purpose computer so that it functions as a special purpose computer to provide a surgery risk service, such as by providing scoring, data analytics and machine-learning to forecast major complications and death after any type of surgery for a patient. In an example embodiment, the systems and methods described herein are configured to provide analytics that are suggestive of a surgery risk score relating to eight major postoperative complications and death up to 24 months after surgery, and/or the like.

In some examples, the systems and methods described herein may ingest or otherwise access input data that represents a patient's perioperative health record found in electronic health records (EHR). In some examples, the systems and methods are configured to evaluate the EHR and/or provide analysis/forecasting complications after surgery for the patient in the form of a score or a personalized risk panel. Accordingly, the provision of a score, personalized risk panel, and/or the like before and/or during surgery are advantageous, in some examples, to correct surgical planning, staffing, execution or the like to advantageously improve the patient's outcome before it starts or while it is in process.

Specifically, and in some examples, the systems and methods disclosed herein are configured to provide a surgery risk algorithm. In some examples, the surgery risk algorithm is built or otherwise instantiated using a perioperative learning system that is trained using a patient's electronic health records and public datasets from the United States Census data. In particular, the perioperative learning system (e.g., a surgery risk analytics platform) is configured to identify one or more extracted features that are suggestive a particular result, such as a score. The system is configured to ingest or otherwise access input data related to a patient's health record. Given said input data, the example systems and methods are configured to output a score, a personalized risk panel, a patient's physiologic response, a recommendation, or the like.

In some embodiments, the score may forecast patient-level probabilistic risk scores for eight major postoperative complications (i.e., acute kidney injury, sepsis, venous thromboembolism, intensive care unit admission>48 hours, mechanical ventilation>48 hours, wound, neurological and cardiovascular complications) and death up to 24 months after surgery. Alternatively or additionally, in some examples, the systems and methods are configured to output a personalized risk panel for the eight major complications and mortality risk at 1, 3, 6, 12, and 24 months after surgery together with a list of the top three features contributing to each of the calculated risk scores. In some examples, recommendations to improve the score such as prevention, additional treatment interventions, etc.

Alternatively or additionally, the systems and methods described herein may further be configured to alter or otherwise modify a patient's personalized risk panel based on input from physicians. For example, the systems and methods may in some examples collects physician feedback for future retraining of the scores produced from the prediction models.

Example System Environment

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Figure 1:
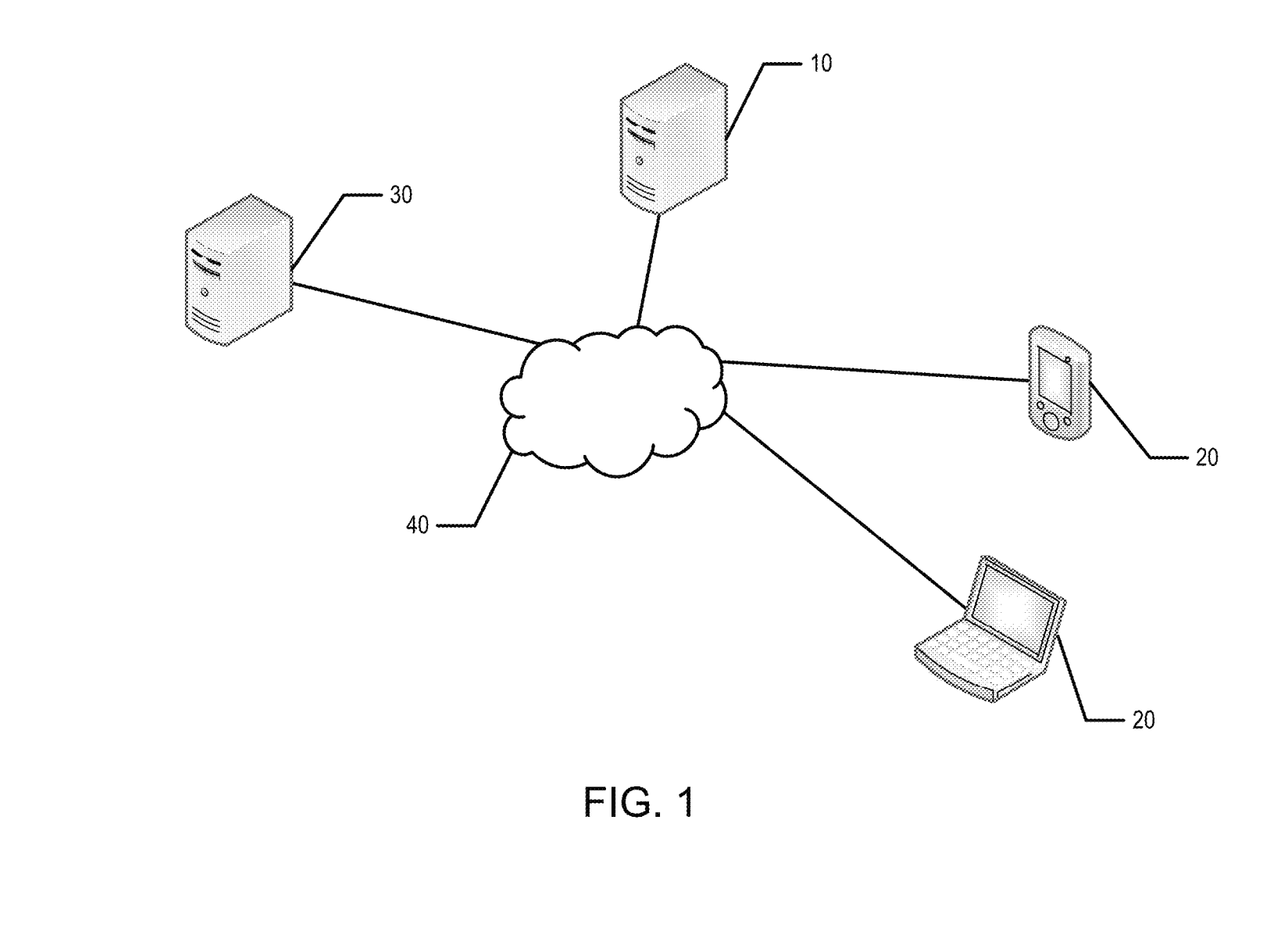
FIG. 1 is an overview of a system that can be used to practice embodiments of the present invention.

FIG. 1 provides an illustration of the components involved in an exemplary embodiment of the present invention. As shown in FIG. 1, this particular embodiment may include one or more surgery risk analytics computing entities 10, one or more user computing entities 20, one or more information/data hosting entities 30, one or more networks 40, and/or the like. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

Figure 2:
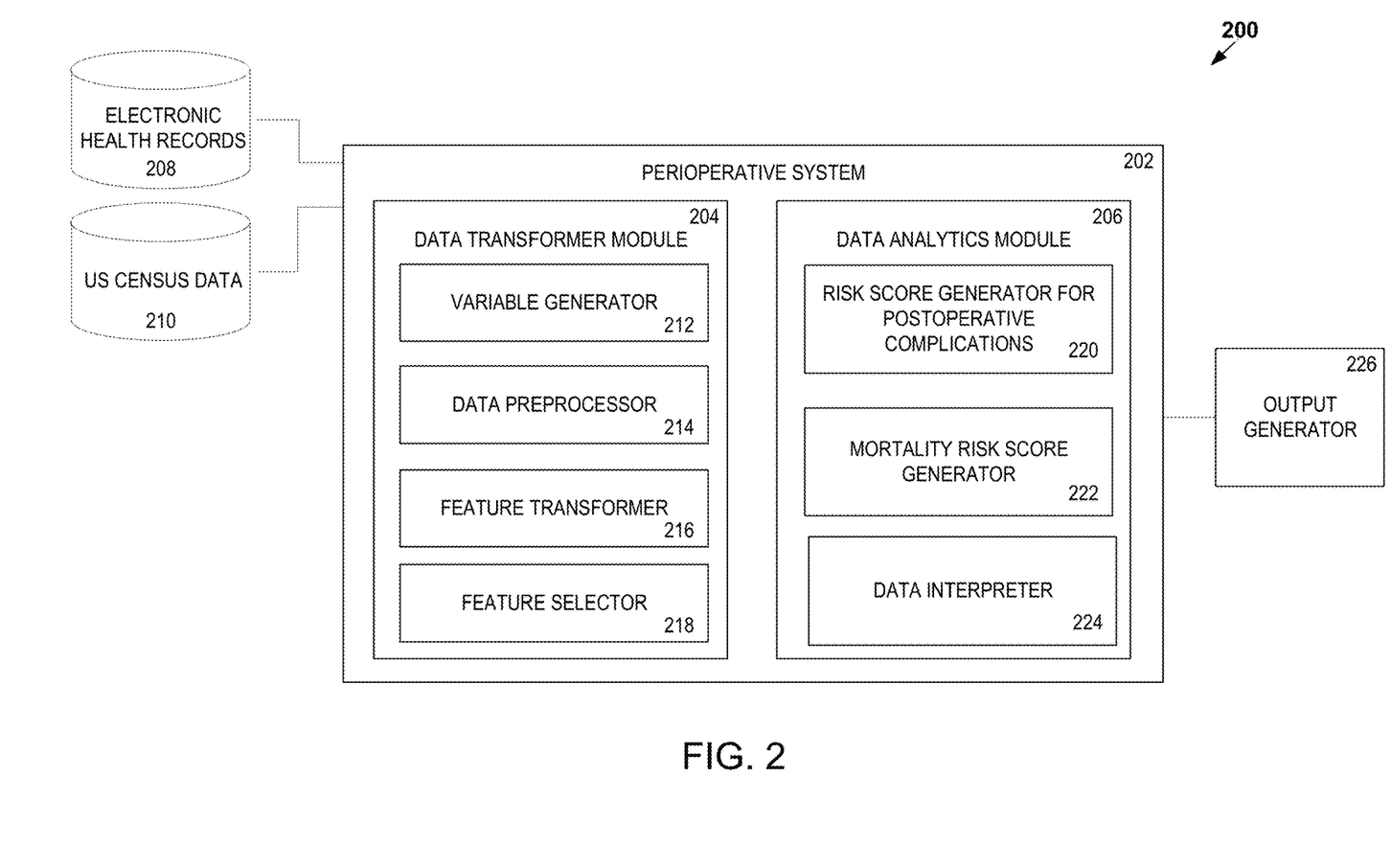
FIG. 2 is an exemplary block diagram of example components of an example surgery risk analytics platform service environment.

FIG. 2 is an example block diagram of example component of an example surgery risk analytics platform environment 200. In some example embodiments, the surgery risk analytics platform environment 200 comprises a perioperative system 202 comprising a data transformer module 204 and a data analytics module 206. In some example embodiments, the surgery risk analytics platform environment 200 further comprises one or more data sources, such as but not limited to, electronic health records 208, US census data 210 and an output generator 226. In some example embodiments, social determinants of health such as data related to income, poverty, etc. may also be accessed and/or otherwise analyzed. The data transformer module 204, data analytics module 206, and output generator 226 make take the form of, for example, a code module, a component, circuitry or the like. The components of the surgery risk analytics platform environment 200 are configured to provide various logic (e.g. code, instructions, functions, routines and/or the like) and/or services related to calculating risk for postoperative complications and death after surgery accurately in the pre-operative period using advanced mathematical and machine learning modeling of clinical data.

In some example embodiments, the data transformer module 204 is configured to input data, such as the data contained in the electronic health records 208 and US Census data 210 to be processed into an optimized dataset for use in calculating risk for postoperative complications and death after surgery. In some embodiments, the data transformer module 204 may store the results into NoSQL database for further interpretation and visualization. Alternatively or additionally the data transformer module 204 may be configured to receive or input data continuously or semi-continuously, such as via a data stream and in real-time. The optimized dataset and one or more features contributing to the risk for an individual patient are configured to be generated by one or more of a variable generator 212, data preprocessor 214, feature transformer 216, and a feature selector 218.

At least one purpose of the data transformer module 204 is to gather all data from different sources such as patients' EHR, US Bureau of Vital Statistics, Social Security Death Index, US Renal Data System, US Census Data, and the like. The data used relates to at least the following categories: patient admission information, provider information, lab tests data, and medication data. After aggregating and collecting the data, the data transformer module 204 transforms them into patient based records stream on the spark streaming infrastructure. The spark streaming periodically pulls the data based on JSON records from Kafka distributed message queue. Thereafter, each patient JSON record is converted into raw features.

The data transformer module 204 then transforms and remodels these raw features based on several predefined dictionaries to fit the input of 8 complications risk prediction models. The 8 complications risk prediction models may be configured to work independently from each other. Additionally or alternatively, the data transformer module 204 is configured to explore the interrelationship among the different complications. In some example embodiments, the data transformer module 204 is configured for batch model training on the distributed machine learning tools of spark, including Mlib for general machine learning tasks, and TensorOnSpark for deep learning tasks to which general data analysis and processing tasks are performed by SparkSQL.

In some example embodiments the variable generator 212 is configured to determine and extract useful perioperative predictor features to be used in calculating risk from 285 available perioperative demographic, socio-economic, administrative, clinical, pharmacy and laboratory variables to be used for the patient. In some example embodiments, patient perioperative comorbidities were derived using up to fifty International Classification of Diseases, Ninth Revision, Clinical Modification (ICD-9-CM).

A data preprocessor 214 is configured to use a set of automatic rules to remove errors and outliers. The data preprocessor 214 is further configured to replace missing nominal variables with a distinct "missing" category while missing continuous variables are replaced by the mean value for a given variable as shown in Table 1.

| Variable | Type of Variable | Data Source | Number of categories | Type of Preprocessing |
|---|---|---|---|---|
| Demographic variables | | | | |
| Age | Continuous | Derived | | Imputation of outliers, Nonlinear function |
| Gender | Binary | Raw | 2 | |
| Race | Nominal | Raw | 5 | Optimization of categorical features |
| Socioeconomic variables | | | | |
| Primary Insurance | Nominal | Raw | 4 | Optimization of categorical features |
| Zip code | Nominal | Raw | 10,000 | Transformation through link to Census data |
| County | Nominal | Raw | 71 | Optimization of categorical features |

-continued

| Variable | Type of Variable | Data Source | Number of categories | Type of Preprocessing |
|---|---|---|---|---|
| Rural Area | Binary | Derived | 2 | |
| Population Proportion Below Poverty | Continuous | Derived | | Obtained using Zip code and linkage to US Census data, Imputation of Outliers |
| Operative Characteristics | | | | |
| Day of Admission | Nominal | Derived | 7 | Optimization of categorical features |
| Month of Admission | Nominal | Derived | 12 | Optimization of categorical features |
| Year of Admission | Nominal | Derived | 11 | Optimization of categorical features |
| Attending surgeon | Nominal | Raw | 520 | Optimization of categorical features |
| Surgery Type | Nominal | Derived | 5 | Optimization of categorical features |
| Comorbidities | | | | |
| Myocardial Infarction | Binary | Derived | 2 | |
| Congestive heart failure | Binary | Derived | 2 | |
| Peripheral Vascular Disease | Binary | Derived | 2 | |
| Cerebrovascular Disease | Binary | Derived | 2 | |
| Chronic Pulmonary Disease | Binary | Derived | 2 | |
| Diabetes | Binary | Derived | 2 | |
| Cancer | Binary | Derived | 2 | |

The feature transformer 216 may then apply feature transformation to reduce dimensionality of the data to decrease overfitting in which categorical and nominal variables with multiple levels (e.g., surgeon's identities and zip codes) are optimized using conditional probabilities for a patient to have a particular variable value conditioned on each outcome separately. The feature transformer 216 is configured to substitute the values $x_i$ of categorical variables with the ratios $\log[P(X_i=x_i|C=1)/P(X_i=x_i|C=0)]$ where $P(X_i=x|C=c)=\#\{j:C^j=c, x_i^j=x\}/\#\{j:C^j=c\}$ and then treat each categorical variable as an ordered variable. In case of classification trees such substitution gives the optimal splits, in terms of cross-entropy or Gini index, such modeling of categorical variables provides less overfitting than when using binary dummy variables. In order to obtain a reliable estimate of $P(X_i=x|C=c)$, categorical risk factors with categories with fewer than 100 records were grouped together and labeled "other". This "other" group was further split into several subgroups where each subgroup contained categories with similar proportions of patients from different classes. This was achieved by performing k-means clustering on the set of categories in the "other" group.

Surgical procedure codes were optimized using forest of trees approach to reduce 4-digit primary procedure ICD-9-CM codes that are prefix-based on anatomical location of surgery and often lack detailed descriptions of surgical approach. Each node represents a group of procedures, with roots representing most general groups of procedures and leaf nodes representing specific procedures.

The feature selector 218 is configured to select features using variance inflation factors to evaluate collinearity and remove highly collinear predictors. The feature selector 218 is configured to taken into account the nature of clinical data and that many predictors are derived from a single attribute thus the likelihood of collinearity among variables is high.

The data analytics module 206 is configured to input the optimized data from the data transformer module 204 and determine how to use the optimized data and selected features to calculate patient-level risk probabilities for each of the eight complications. Subsequently, the calculated risk probabilities are used as input data for calculating mortality scores, which are displayed graphically by the output generator 226. In some example embodiments, the data analytics module 206 comprises a risk score generator for postoperative complications 220, a mortality risk score generator 222, and a data interpreter 224. Additionally, the data analytics module 206 is configured to provide batched model training with distributed machine learning/deep learning tools, and SQL based data analysis.

In some example embodiments, the risk score generator for postoperative complications 220 may be configured to calculate patient-level risk scores, representing the probability of each complication during hospitalization after index surgery, and calculated using a generalized additive model (GAM) with a logistic link function:

$$\text{logit } P(C = 1 \mid X = x) = \alpha + \sum_{i=1}^{m} f_i(x_i),$$

where m is the number of risk factors, $X=(X_1, K, X_m)$ are the risk factors, $x=(x_1, K, x_m)$ are the values of these factors, $f_i$ is a nonlinear risk function associated with the ith risk factor and $\alpha$ is a free term. Nonlinear risk functions $f_i$ were estimated for each feature with cubic splines via a local scoring algorithm. The degrees of freedom for each spline were estimated by maximizing restricted likelihood function. Degrees of freedom characterize a curvature of a spline, with value 1 corresponding to a linear function. Risk predictors with estimated degrees of freedom close to 1 were not smoothed in the final model; instead the original values of risk predictors $x_i$ were used. Therefore, the final model has the following form as in equation that follows where $I$ is a set of risk predictors with estimated degrees of freedom close to 1 and $w_i$ is the linear weight of the $i^{th}$ risk predictors:

$$logit\ P(E = 1 \mid X = x) = \alpha + \sum_{i \in I} w_i * x_i + \sum_{i \in \bar{I}} f_i(x_i).$$

The risk score generator for postoperative complications 220 may be further configured to, for each complication separately, define the optimal cutoff values that best categorize patients into low and high risk categories using risk probabilities calculated by the GAM algorithm. The most important features contributing to the risk for an individual patient were derived based on how different she or he is from the patient with an "average" risk. For each complication, model produces the predicted surgery risk score along with the important contributing risk factors. The output risk scores categorize patients into low-risk and high-risk groups by employing a threshold cutoff value.

Figure 6:
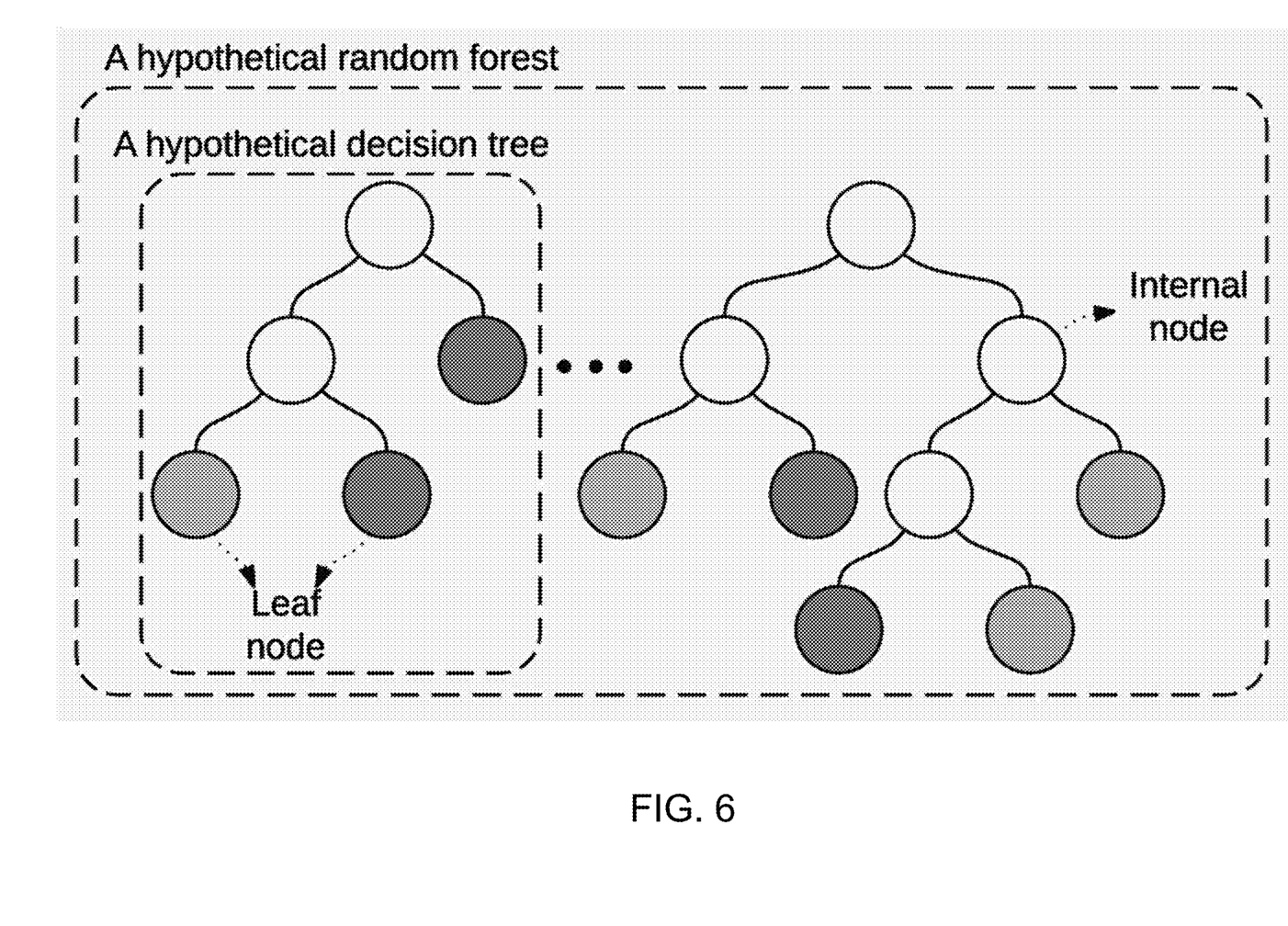
FIG. 6 is an exemplary schematic diagram of a random forests (RF) classifier.

In some example embodiments, the mortality risk score generator 222 may be configured to calculate patient-level mortality scores, representing the probability of death at 1, 3, 6, 12, and 24 months after index surgery using a random forests (RF) classifier trained over the individual complication risk probabilities within a 5-fold cross validation design. Random forests (RF) is a machine learning method which generates and uses a collection of numerous classification and regression trees (CART) and aggregates their results. Each of the generated classifiers are trained on a bootstrap sample of the training data. Each generated tree in the random forests predicts the outcome and then the model generates the final outcome through aggregating the outcomes of all trees using majority voting of the trees as shown in FIG. 6. Random forests employ bootstrap aggregation and random feature selection to construct a set of decision trees, thus, applying controlled variation. The R implementation of the random forests classifier is used and the mean decrease in accuracy measure to determine the features importance. In some embodiments, the feature is determined to be more important if removing it from the random forests causes more decrease of the model accuracy.

The mortality risk score generator 222 may be further configured to automatically tune the parameters for each classifier through maximizing accuracy as the cross validation performance score over searching a parameter space.

A data interpreter, such as data interpreter 224, may then be configured to input the patient-level risk and mortality scores and determine the top three features contributing to each of the calculated scores.

The scores may be input into the output generator 226 to enable the generation of a graphical output and/or a personalized risk panel for the eight major complications and mortality risk at 1, 3, 6, 12, and 24 months after surgery together with the list of the top three features contributing to each of the calculated scores. In some example embodiments, the graphical output and/or personalized risk panel is provided to physicians for feedback on the risk assessment.

In some example embodiments, the surgery risk analytics platform provides for two clients for physicians to conveniently access and interact with the platform in any moment. The clients include a mobile app client and web client, both exchange information via RestAPI. The mobile app client implements on any mobile operating system and contains functionality of pushing notifications through cloud messaging to physicians once information and/or results of their patients are available. The mobile app client and web client provides physicians a series of services to facilitate them monitoring the immediate surgery risks of their patients such as email notification for the new status of patients, the patients' profile generation, and one or more visualizations of each predicted surgery risk scores.

Based on the sensitivity of patient health information, information security is an essential part of the surgery risk analytics platform. The surgery risk analytics platform applies the public key infrastructure (PKI) to protect the exchange of the sensitive health information. Data exchanging is encrypted through the Secure Sockets Layer (SSL) protocol and only the intended receiver can decipher the data by using the private key it possesses. Additionally and in some embodiments, RestAPI is applied for clients to communicate with the surgery risk analytics platform.

Example Computing Device Architecture

Figure 3:
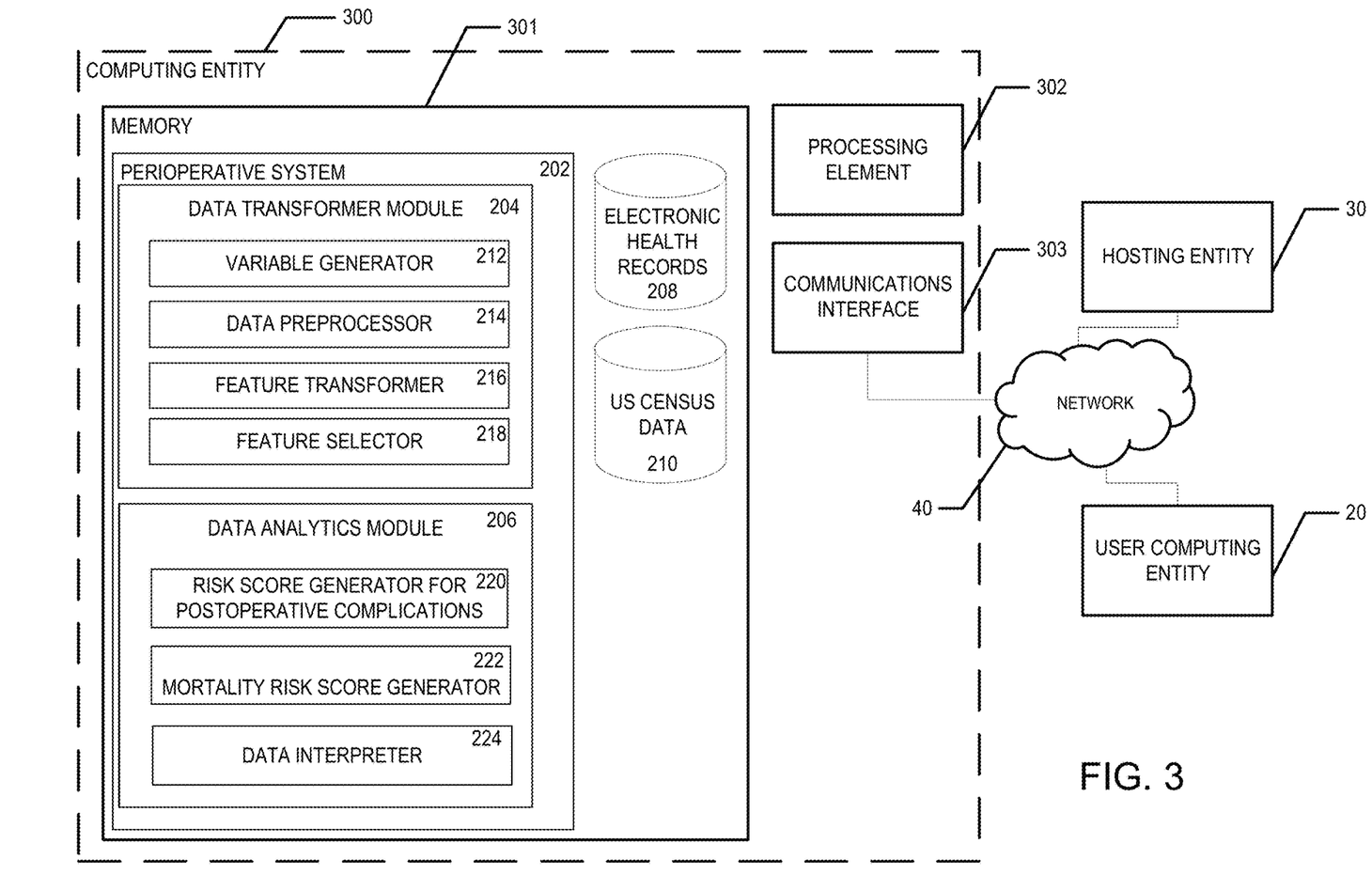
FIG. 3 is an exemplary block diagram of an example computing device for practicing embodiments of the surgery risk analytics platform service.

FIG. 3 is an example block diagram of an example computing device for practicing embodiments of an example surgery risk analytics platform environment. In particular, FIG. 3 shows a computing entity 300 that may be utilized to implement a surgery risk analytics platform environment 200 having a perioperative system 202. One or more general purpose or special purpose computing systems/devices may be used to implement the perioperative system 202. In addition, the computing entity 300 may comprise one or more distinct computing systems/devices and may span distributed locations. For example, in some embodiments, the surgery risk analytics platform environment 200 may be accessible remotely via the network 40. In other example embodiments, one or more of the perioperative system 202 may be configured to operate remotely. In some example embodiments, a data transformer module 204, data analytics module 206, or other module that requires heavy computational load may be configured to perform that computational load and thus may be on a remote device or server. Furthermore, each block shown may represent one or more such blocks as appropriate to a specific example embodiment. In some cases one or more of the blocks may be combined with other blocks. Also, the perioperative system 202 may be implemented in software, hardware, firmware, or in some combination to achieve the capabilities described herein.

In the example embodiment shown, computing entity 300 comprises a computer memory ("memory") 301, a communications interface 303, one or more processing elements 302, input/output devices (e.g., keyboard, mouse, CRT or LCD display, touch screen, gesture sensing device and/or the like), other computer-readable media. The processing element 302 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 3 as a single processor, in some embodiments the processor 302 comprises a plurality of processors. The plurality of processors may be in operative communication with each other and may be collectively configured to perform one or more functionalities of the graphical annotation environment as described herein.

The perioperative system 202, electronic health records 208, and US Census data 210 are shown residing in memory 301. The memory 301 may comprise, for example, transitory and/or non-transitory memory, such as volatile memory, non-volatile memory, or some combination thereof. Although illustrated in FIG. 3 as a single memory, the memory 301 may comprise a plurality of memories. The plurality of memories may be embodied on a single computing device or may be distributed across a plurality of computing devices collectively configured to function as the graphical annotation environment. In various example embodiments, the memory 301 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof.

In general, the terms computing entity, computer, entity, device, system, and/or similar words used herein interchangeably may refer to, for example, one or more computers, computing entities, desktops, mobile phones, tablets, phablets, notebooks, laptops, distributed systems, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

In one embodiment, the computing entity 300 may also include one or more communications interfaces 303 for communicating with various other computing entities, such as by communicating data, content, information, and/or similar terms used herein interchangeably that can be transmitted, received, operated on, processed, displayed, stored, and/or the like.

As shown in FIG. 3, in one embodiment, the computing entity 300 may include or be in communication with one or more processing elements 302 (also referred to as processors, processing circuitry, and/or similar terms used herein interchangeably) that communicate with other elements within the analysis computing entity 10 via a bus, for example. As will be understood, the computing entity 300 may be embodied in a number of different ways. For example, the computing entity 300 may be embodied as one or more complex programmable logic devices (CPLDs), microprocessors, multi-core processors, co-processing entities, application-specific instruction-set processors (ASIPs), microcontrollers, and/or controllers. Further, the processing element 302 may be embodied as one or more other processing devices or circuitry. The term circuitry may refer to an entirely hardware embodiment or a combination of hardware and computer program products. Thus, the processing element 302 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 302 may be configured for a particular use or configured to execute instructions stored in volatile or non-volatile media or otherwise accessible to the processing element 302. As such, whether configured by hardware or computer program products, or by a combination thereof, the processing element 302 may be capable of performing steps or operations according to embodiments of the present invention when configured accordingly.

In one embodiment, the computing entity 10 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 301, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the computing entity 300 may further include or be in communication with volatile media (also referred to as volatile storage, memory, memory storage, memory circuitry and/or similar terms used herein interchangeably). In one embodiment, the volatile storage or memory may also include one or more volatile storage or memory media, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 302. Thus, the databases, database instances, database management systems, data, applications, programs, program modules, scripts, source code, object code, byte code, compiled code, interpreted code, machine code, executable instructions, and/or the like may be used to control certain aspects of the operation of the computing entity 300 with the assistance of the processing element 302 and operating system.

As indicated, in one embodiment, the computing entity 300 may also include one or more communications interfaces 303 for communicating with various other computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analysis computing entity 10 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown in FIG. 3, the computing entity 300 may also comprise a user interface (that can include a display coupled to a processing element). For example, the user interface may include or be in communication with one or more input elements, such as a keyboard input, a mouse input, a touch screen/display input, motion input, movement input, audio input, pointing device input, joystick input, keypad input, and/or the like. The computing entity 300 may also include or be in communication with one or more output elements (not shown), such as audio output, video output, screen/display output, motion output, movement output, and/or the like. These input and output elements may include software components such as a user application, browser, graphical user interface, and/or the like to facilitate interactions with and/or cause display of information/data from the computing entity 300, as described herein. The user input interface can comprise any of a number of devices or interfaces allowing the computing entity 300 to receive data, such as a keypad (hard or soft), a touch display, voice/speech or motion interfaces, or other input device. In embodiments including a keypad, the keypad can include (or cause display of) the conventional numeric (0-9) and related keys (#, *), and other keys used for operating the user computing entity 20 and may include a full set of alphabetic keys or set of keys that may be activated to provide a full set of alphanumeric keys.

As will be appreciated, one or more of the components of the computing entity 300 may be located remotely from other components of the computing entity 300, such as in a distributed system. Furthermore, one or more of these components may be combined with additional components to perform various functions described herein, and these additional components may also be included in the computing entity 300. Thus, the computing entity 300 can be adapted to accommodate a variety of needs and circumstances. As will be recognized, these architectures and descriptions are provided for exemplary purposes only and are not limiting to the various embodiments.

The perioperative system 202 may interact with the network 40, via the communications interface 303, with information/data hosting entity 30 and/or user computing entity 20. The network 40 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX, Bluetooth) that facilitate communication between remotely situated humans and/or devices. In some instance the network 40 may take the form of the internet or may be embodied by a cellular network such as an LTE based network. In this regard, the communications interface 303 may be capable of operating with one or more air interface standards, communication protocols, modulation types, access types, and/or the like. The user computing entity 20 include desktop computing systems, notebook computers, mobile phones, smart phones, personal digital assistants, tablets and/or the like.

In various embodiments, a user computing entity 20 may be configured to exchange and/or store information/data with the computing entity 300. For instance, the user computing entity 20 may be used by a user (e.g., a scientist, lab technician or the like) to provide instructions to the computing entity 300 for structuring or modifying the analysis to be performed by the computing entity 300. The user computing entity 20 may additionally or alternatively receive information/data from the computing entity 300 or an information/data hosting entity 30 regarding results produced from the operations performed by the computing entity 300.

In one embodiment, the user computing entity 20 may include one or more components that are functionally similar to those of the computing entity 300 described above. For example, in one embodiment, each user computing entity 20 may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

In various embodiments, the information/data hosting entity 30 may be configured to receive, store, and/or provide information/data needed for predicting complications after surgery utilizing the above-described an automated analytics framework.

In one embodiment, an information/data hosting entity 30 may include one or more components that are functionally similar to those of the computing entity 300, user computing entity 20, and/or the like. For example, in one embodiment, each information/data hosting entity 30 may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

Example embodiments of the present invention provide tools for predicting complications after surgery. Certain example embodiments utilize an automated analytics framework to implement a perioperative risk algorithm that uses existing clinical data in electronic health records to forecast patient-level probabilistic risk scores for eight major postoperative complications (acute kidney injury, sepsis, venous thromboembolism, intensive care unit admission>48 hours, mechanical ventilation>48 hours, wound, neurologic and cardiovascular complications). Some of these example embodiments may thereafter determine patient-level mortality probabilities using the calculated risk scores.

Example Operations for Generating a Personalized Risk Panel

Figure 4:
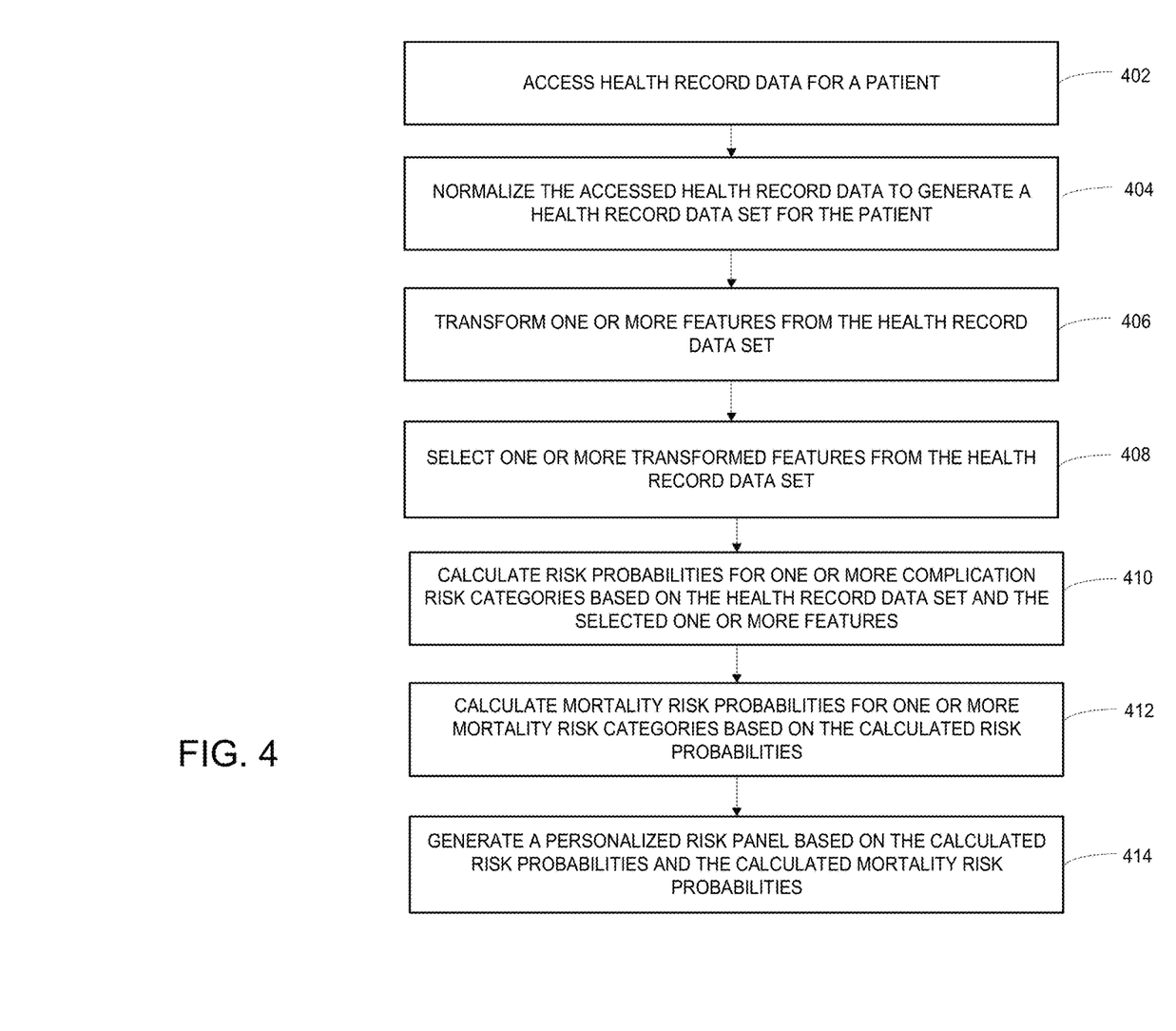
FIG. 4 is a flowchart illustrating an example method for the surgery risk analytics platform service.

FIG. 4 illustrates an example flowchart of the operations performed by an apparatus, such as computing entity 300 of FIG. 3, to evaluate surgical risk and generate a personalized risk panel.

As is shown in step/operation 402, the apparatus may include means, such as the data transformer module 204, the processing element 302, or the like, for accessing health record data for a patient. Alternatively or additionally other public data may be used. For example, using a residency zip code, a patient's residing neighborhood characteristics and distance from a hospital may be calculated and factor into scoring risk.

As shown in step/operation 404, the apparatus may include means, such as the data transformer module 204, the data preprocessor 214, the processing element 302, or the like, for normalizing the accessed health record data to generate a health record data set for the patient. In some example embodiments normalizing the access health record data involves using a set of automatic rules to remove errors and outliers to aid in the generation of the personalized risk panel.

As shown in step/operation 406, the apparatus may include means, such as the data transformer module 204, the variable generator 212, the feature transformer 216, the processing element 302, or the like, for transforming one or more features from the health record data set. The one or more features may contribute to each of the calculated risk scores. In some example embodiments, transforming features from any native electronic health record data format to the processed dataset optimized for use in predictive risk modeling comprises replacing missing variable features with a distinct "missing" category while missing continuous variables are replaced by the mean value for a given feature variable.

As shown in step/operation 408, the apparatus may include means, such as the data transformer module 204, the feature selector 208, the processing element 302, or the like, for selecting one or more features from the health record data set. In some example embodiments, the selection uses variance inflation factors to evaluate collinearity and remove highly collinear predictors.

As shown in step/operation 410, the apparatus may include means, such as the data analytics module 206, the risk score generator for postoperative complications 220, the processing element 302, or the like, for calculating risk probabilities for one or more complication risk categories based on the health record data set and the selected one or more features. In some example embodiments, patient-level risk scores representing the probability for each complication during hospitalization after index surgery are calculated using a generalized additive model (GAM) with logistic link function. All models are adjusted for nonlinearity of all covariates using nonlinear risk functions estimated with cubic spines. Additionally, for each complication separately, risk probabilities calculated by the GAM algorithm are used to define the optimal cutoff values that best categorize patients into low and high risk categories by maximizing the Youden index. The most important features contributing to the risk for an individual patient were derived based on how different she or he is from the patient with an "average" risk.

As shown in step/operation 412, the apparatus may include means, such as the data analytics module 206, the mortality risk score generator 222, the processing element 302, or the like, for calculating mortality risk probabilities for one or more mortality risk categories based on the calculated risk probabilities. In some example embodiments, patient-level mortality scores representing the probability of death at 1, 3, 6, 12, and 24 months after index surgery are calculated using a random forests classifier trained over the individual complication risk probabilities within a 5-fold cross validation design. In some embodiments, the apparatus may include means, such as the data analytics module 206, the mortality risk score generator 222, the processing element 302, or the like, for automatically tuning the parameters for each classifier through maximizing accuracy as the cross validation performance score over searching a parameter space.

Figure 5A:
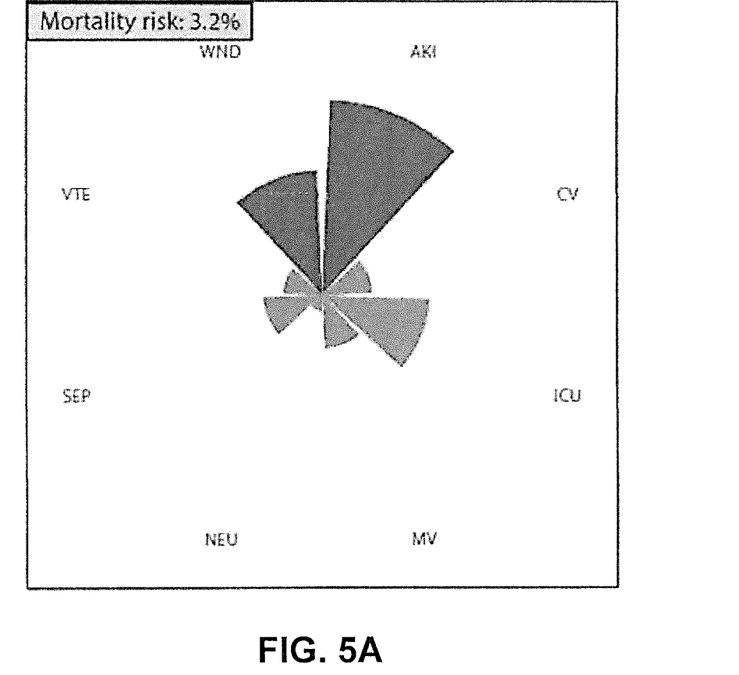
FIGS. 5A and 5B is an exemplary schematic diagram of a personalized risk panel according to one embodiment of the present invention.
Figure 5B:
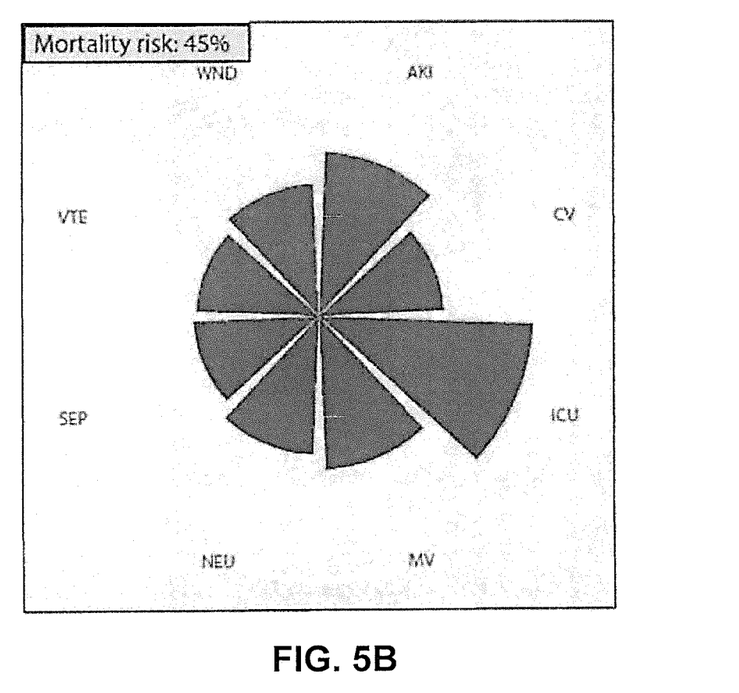

And finally, as shown in step/operation 414, the apparatus may include means, such as the data analytics module 206, the data interpreter 224, the processing element 302, or the like, for generating a personalized risk panel based on the calculated risk probabilities and the calculated mortality risk probabilities. In some example embodiments, the personalized risk panel is configured to utilize the calculated complication risk scores and the mortality risk scores to display the eight major complications at 1, 3, 6, 12, and 24 months after surgery together with an indication of the top three features contributing to each of the calculated risk scores as shown in FIGS. 5A and 5B. The pie charts of FIGS. 5A and 5B provide risk scores of a patient for postoperative complications including acute kidney injury, cardiovascular complications, intensive care unit admission>48 hours, mechanical ventilation>48 hours, neurological complications, sepsis, venous thromboembolism, and wound complications.

It will be understood that each block of the flowchart shown in FIG. 4, and combinations of blocks in the flowchart, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 301 of an apparatus employing an embodiment of the present invention and executed by a processor 302 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIG. 4, when executed, convert a computer or processing circuitry into a particular machine configured to perform an example embodiment of the present invention. Accordingly, the operations of FIG. 4 define an algorithm for configuring a computer or processor, to perform an example embodiment. In some cases, a general purpose computer may be provided with an instance of the processor which performs the algorithm of FIG. 4 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowcharts', and combinations of blocks in the flowchart, can be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included (some examples of which are shown in dashed lines in FIG. 4). It should be appreciated that each of the modifications, optional additions or amplifications described herein may be included with the operations herein either alone or in combination with any others among the features described herein.

In some embodiments, the surgery risk analytics platform is a part of an idealist platform. The idealist platform is a scalable, modular and exportable artificial intelligence (AI) predictive analytics platform for medical decision making designed for implementation in health care environment without disruption of clinical work flow. The idealist platform can use any kind of real-time data, including electronic health records and streaming medical device data in secure, HIPPA compliant fashion. The idealist platform can deploy any type of machine learning algorithm, including deep learning, as a plug and play module and provide interactive output for physician users. The platform uses patient's digital medical footprint of all available unique data elements, some of which are measured every few milliseconds, and using AI can predict and display patient's clinical status for variety of conditions. The platform can also identify deviations from the patient's foreseen medical outcomes, help to determine if the patient's level of care should be altered, and assists with resource allocation. The platform allows advanced machine learning models to evolve and refine over time using not only new data abut also physicians input.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A surgery risk analytics system for surgical risk evaluation based at least in part on a surgery risk analytics platform service, the surgery risk analytics system comprising a processor and a memory having computer coded instructions therein when executed by the processor, cause the surgery risk analytics system to:

receive, using a data transformer module, health record data associated with monitoring of a patient for surgery risks via a client device, the health record data comprising a plurality of variables associated with a plurality of features, the plurality of features comprising a plurality of perioperative predictor features;

normalize, using the data transformer module, the received health record data by replacing missing values of one or more of the plurality of variables with replacement values based at least in part on variable type and by preprocessing the one or more of the plurality of variables based at least in part on respective one or more of a plurality of preprocessing types associated with the one or more of the plurality of variables;

transform, using the data transformer module, one or more of the plurality of features by optimizing the plurality of variables based at least in part on one or more conditional properties associated with a plurality of outcomes, thereby conforming the plurality of variables with inputs of a plurality of predictive models of a data analytics module based at least in part on the optimizing, wherein the plurality of variables are optimized by substituting the plurality of variables with probability ratios associated with ordered variables, wherein each of the plurality of predictive models is associated with a given complication risk and is configured to (i) generate one or more complication risk probabilities based at least in part on the one or more transformed features and (ii) execute independently from other ones of the plurality of predictive models;

select, using the data transformer module, the one or more transformed features based at least in part on variance factors of the one or more transformed features, the variance factors comprising a likelihood of excessive collinearity;

generate, using the plurality of predictive models, a plurality of complication risk probabilities for a plurality of respective complication risks associated with the plurality of predictive models based at least in part on the health record data and the selected one or more features;

generate, using one or more trained machine learning classifier models of the data analytics module, one or more mortality risk probabilities at given future times after a surgery event, wherein (i) the one or more trained machine learning classifier models comprises a plurality of random forest classifiers that are trained to generate a plurality of predictions associated with respective ones of the plurality of outcomes based at least in part on training data comprising the plurality of complication risk probabilities and (ii) the one or more mortality risk probabilities comprise an aggregation of the plurality of predictions;

generate, using an output generator, a user interface configured to render a personalized risk panel for the patient based at least in part on the plurality of complication risk probabilities and the one or more mortality risk probabilities; and transmit the personalized risk panel from the output generator to the client device for graphical output on a client application executing on the client device, wherein (i) the personalized risk panel comprises results of the monitoring and a determination of level of care based at least in part on the plurality of complication risk probabilities and the one or more mortality risk probabilities and (ii) the personalized risk panel is associated with a surgery risk analytics platform that is configured for medical decision making associated with modifying surgical planning or staffing before or during surgery on the patient based at least in part on the personalized risk panel.

2. The surgery risk analytics system of claim 1, wherein the computer coded instructions, when executed by the processor, further cause the data transformer module to:
remove one or more outliers from the health record data;
replace the one or more missing variables with replacement data; and
normalize the health record data to generate a health record data for the patient.

3. The surgery risk analytics system of claim 1, wherein the plurality of features comprise one or more of perioperative demographic, socio-economic, administrative, clinical, pharmacy, or laboratory variables.

4. The surgery risk analytics system of claim 1, wherein the computer coded instructions, when executed by the processor, further cause the data analytics module to:
generate the plurality of complication risk probabilities using a generalized additive model (GAM) with logistic link function; and
define one or more complication risk categories based at least in part on the GAM.

5. The surgery risk analytics system of claim 1, wherein the computer coded instructions, when executed by the processor, further cause the data analytics module to:
apply a random forests classifier model of the one or more trained machine learning classifier models over the plurality of complication risk probabilities to identify probability of death at one, three, six, twelve, and twenty four months after surgery.

6. The surgery risk analytics system of claim 1, wherein the personalized risk panel comprises a list of features contributing to the plurality of complication risk probabilities.

7. The surgery risk analytics system of claim 1, wherein transforming, using the data transformer module, the plurality of features comprises remodeling raw features based at least in part on a plurality of predefined dictionaries for use in the plurality of predictive models.

8. A method for evaluating surgical risk and providing a surgery risk analytics platform service, the method comprising:
receiving, by a data transformer module, health record data associated with monitoring of a patient for surgery risks via a client device, the health record data comprising a plurality of variables associated with a plurality of features, the plurality of features comprising a plurality of perioperative predictor features;
normalizing, by the data transformer module, the health record data by replacing missing values of one or more of the plurality of variables with replacement values based at least in part on variable type and by preprocessing the one or more of the plurality of variables based at least in part on respective one or more of a plurality of preprocessing types associated with the one or more of the plurality of variables;
transforming, by the data transformer module, one or more of the plurality of features by optimizing the plurality of variables based at least in part on one or more conditional properties associated with a plurality of outcomes, thereby conforming the plurality of variables with inputs of a plurality of predictive models of a data analytics module based at least in part on the optimizing, wherein the plurality of variables are optimized by substituting the plurality of variables with probability ratios associated with ordered variables, wherein each of the plurality of predictive models is associated with a given complication risk and is configured to (i) generate one or more complication risk probabilities based at least in part on the one or more transformed features and (ii) execute independently from other ones of the plurality of predictive models;
selecting, by the data transformer module, the one or more transformed features based at least in part on variance factors of the one or more transformed features, the variance factors comprising a likelihood of excessive collinearity;
generating, using the plurality of predictive models, a plurality of complication risk probabilities for a plurality of respective complication risks associated with the plurality of predictive models based at least in part on the health record data and the selected one or more features;
generating, using one or more trained machine learning classifier models of the data analytics module, one or more mortality risk probabilities at given future times after a surgery event, wherein (i) the one or more trained machine learning classifier models comprises a plurality of random forest classifiers that are trained to generate a plurality of predictions associated with respective ones of the plurality of outcomes based at least in part on training data comprising the plurality of complication risk probabilities and (ii) the one or more mortality risk probabilities comprise an aggregation of the plurality of predictions;
generating, by an output generator, a user interface configured to render a personalized risk panel for the patient based at least in part on the plurality of complication risk probabilities and the one or more mortality risk probabilities; and
transmitting the personalized risk panel from the output generator to the client device for graphical output on a client application executing on the client device, wherein (i) the personalized risk panel comprises results of the monitoring and a determination of level of care based at least in part on the plurality of complication risk probabilities and the one or more mortality risk probabilities and (ii) the personalized risk panel is associated with a surgery risk analytics platform that is configured for medical decision making associated with modifying surgical planning or staffing before or during surgery on the patient based at least in part on the personalized risk panel.

9. The method for evaluating surgical risk and providing a surgery risk analytics platform service of claim 8, further comprising:
removing one or more outliers from the health record data;
replacing the one or more missing variables with replacement data; and
normalizing the health record data to generate a health record data for the patient.

10. The method for evaluating surgical risk and providing a surgery risk analytics platform service of claim 8, wherein the plurality of features comprise one or more of perioperative demographic, socio-economic, administrative, clinical, pharmacy, or laboratory variables.

11. The method for evaluating surgical risk and providing a surgery risk analytics platform service of claim 8, further comprising:
   using a generalized additive model (GAM) with logistic link function in generating the plurality of complication risk probabilities; and
   defining one or more complication risk categories based at least in part on the GAM.

12. The method for evaluating surgical risk and providing a surgery risk analytics platform service of claim 8, further comprising: applying a random forests classifier model of the one or more trained machine learning classifier models over the plurality of complication risk probabilities to identify probability of death at one, three, six, twelve, and twenty four months after surgery.

13. The method for evaluating surgical risk and providing a surgery risk analytics platform service of claim 8, wherein the personalized risk panel comprises a list of features contributing to the plurality of complication risk probabilities.

14. The method for evaluating surgical risk and providing a surgery risk analytics platform service of claim 8, wherein transforming the plurality of features comprises remodeling raw features based at least in part on a plurality of predefined dictionaries for use in the plurality of predictive models.

15. A computer program product comprising at least one non-transitory computer-readable storage medium having computer-executable program code portions stored therein, the computer-executable program code portions comprising program code instructions that, when executed, cause an apparatus to:
   receive, using a data transformer module, health record data associated with monitoring of a patient for surgery risks via a client device, the health record data comprising a plurality of variables associated with a plurality of features, the plurality of features comprising a plurality of perioperative predictor features;
   normalize, using the data transformer module, the received health record data by replacing missing values of one or more of the plurality of variables with replacement values based at least in part on variable type and by preprocessing the one or more of the plurality of variables based at least in part on respective one or more of a plurality of preprocessing types associated with the one or more of the plurality of variables;
   transform, using the data transformer module, one or more of the plurality of features by optimizing the plurality of variables based at least in part on one or more conditional properties associated with a plurality of outcomes, thereby conforming the plurality of variables with inputs of a plurality of predictive models of a data analytics module based at least in part on the optimizing, wherein the plurality of variables are optimized by substituting the plurality of variables with probability ratios associated with ordered variables, wherein each of the plurality of predictive models is associated with a given complication risk and is configured to (i) generate one or more complication risk probabilities based at least in part on the one or more transformed features and (ii) execute independently from other ones of the plurality of predictive models;
   select, using the data transformer module, the one or more transformed features based at least in part on variance factors of the one or more transformed features, the variance factors comprising a likelihood of excessive collinearity;
   generate, using the plurality of predictive models, a plurality of complication risk probabilities for a plurality of respective complication risks associated with the plurality of predictive models based at least in part on the health record data and the selected one or more features;
   generate, using one or more trained machine learning classifier models of the data analytics module, one or more mortality risk probabilities at given future times after a surgery event, wherein (i) the one or more trained machine learning classifier models comprises a plurality of random forest classifiers that are trained to generate a plurality of predictions associated with respective ones of the plurality of outcomes based at least in part on training data comprising the plurality of complication risk probabilities and (ii) the one or more mortality risk probabilities comprise an aggregation of the plurality of predictions; and
   generate, using an output generator, a user interface configured to render a personalized risk panel for the patient based at least in part on the plurality of complication risk probabilities and the one or more mortality risk probabilities; and
   transmit the personalized risk panel from the output generator to the client device for graphical output on a client application executing on the client device, wherein (i) the personalized risk panel comprises results of the monitoring and a determination of level of care based at least in part on the plurality of complication risk probabilities and the one or more mortality risk probabilities and (ii) the personalized risk panel is associated with a surgery risk analytics platform that is configured for medical decision making associated with modifying surgical planning or staffing before or during surgery on the patient based at least in part on the personalized risk panel.

16. The computer program product of claim 15, wherein the program code instructions, when executed, further cause the apparatus to:
   remove one or more outliers from the health record data;
   replace the one or more missing variables with replacement data; and
   normalize the health record data to generate a health record data for the patient.

17. The computer program product of claim 15, wherein the plurality of features comprise one or more of perioperative demographic, socio-economic, administrative, clinical, pharmacy, or laboratory variables.

18. The computer program product of claim 15, wherein the program code instructions, when executed, further cause the apparatus to:
   use a generalized additive model (GAM) with logistic link function in generating the plurality of complication risk probabilities; and
   define one or more complication risk categories based at least in part on the GAM.

19. The computer program product of claim 15, wherein the program code instructions, when executed, further cause the apparatus to apply a random forests classifier model of the one or more trained machine learning classifier models over the plurality of complication risk probabilities to identify probability of death at one, three, six, twelve, and twenty four months after surgery.

20. The method of claim 1, wherein the variable type comprises one of a continuous variable type, a binary variable type, or a nominal variable type.

* * * * *